United States Patent [19]
Inouye et al.

[11] Patent Number: 5,191,063
[45] Date of Patent: Mar. 2, 1993

[54] PRODUCTION OF BIOLOGICALLY ACTIVE POLYPEPTIDES BY TREATMENT WITH AN EXOGENOUS PEPTIDE SEQUENCE

[75] Inventors: Masayori Inouye, Bridgewater; Yoshiji Ohta, Highland Park; Xueli Zhu, Iselin; Frank Jordan, Chatham, all of N.J.

[73] Assignee: University of Medicine and Dentistry of New Jersey, N.J.

[21] Appl. No.: 346,552

[22] Filed: May 2, 1989

[51] Int. Cl.$^5$ .................. C07K 3/00; C07K 13/00; C12N 9/00
[52] U.S. Cl. .................. 530/324; 530/326; 530/345; 530/427; 435/839; 935/48; 935/49
[58] Field of Search ............ 530/324, 326, 345, 427; 435/839; 935/48, 49

[56] References Cited

U.S. PATENT DOCUMENTS

| | | | |
|---|---|---|---|
| 4,766,205 | 8/1988 | Ghosh-Dastidar | 530/345 |
| 4,835,251 | 5/1989 | Burnier | 530/324 |
| 4,923,967 | 5/1990 | Bobbitt | 530/427 |

OTHER PUBLICATIONS

Kato, I & Anfinsen, C. B. (1969) *J. Biol. Chem.*, 244 1004–1007 "On the Stabilization of Ribonuclease S--Protein by Ribonuclease S-Peptide".
Markland, F. S., Jr., and Smith, M. L. (1971) in *The Enzymes*, (Boyer, P. D., ed.) vol. 3, pp. 561-608, Academic Press, New York.
Ann. Rev. Biochem., 44, 295 (1975), Zabin and Villarejo, "Protein Complementation".
Biochem., J., 128, 737–749 (1972), C. B. Anfinsen, "Formation and Stabilization of Protein Structure".
Cell, 48, 185–191 (Jan. 30, 1987), Jorgensen et al., "Recognition Site Directing Vitamin K-Dependent [gamma]-Carboxylation Resides on the Propeptide of Factor IX".
Chemical & Engineering News, 32-54 (Apr. 10, 1989), Jonathan King, "Deciphering the Rules of Protein Folding".
J. Biochem., 87, 891-898 (1980), Sakai et al., "Importance of the Carboxyl-Terminal Four Amino Acid Residues in the Inhibitory Activity of Streptomyces Subtilisin Inhibitor (With a Revision of its Carboxyl-Terminal Sequence)".
Journal of Biological Chemistry, 244, 1004–1007 (Feb. 25, 1969), Kato and Anfinsen, "Stabilization of Ribonuclease S-Protein by Ribonuclease S-Peptide".
Journal of Biological Chemistry, 261, 10176-10181 (Aug. 5, 1986), Wong and Doi, "Determination of the Signal Peptidase Cleavage Site in the Preprosubtilisin of *Bacillus subtilis*".
Journal of Biological Chemistry, 261 10482-10484 (Aug. 15, 1986), Wu et al., "Evidence for Pretranslational Regulation of Collagen Synthesis by Procollagen Propeptides".
Journal of Biological Chemistry, 262, 7859-7864 (Jun. 5, 1987), Ikemura et al., "Requirement of Pro-Sequence for the Production of Active Subtilisin E in *Escherichia coli*".
Journal of Biological Chemistry, 262, 15334–15337 (Nov. 15, 1987), Knobloch and Suttie, "Vitamin K-Dependent Carboxylase".
Journal of Biological Chemistry, 262, 17221–17230 (Dec. 15, 1987), Folz and Gordon, "Effects of Deleting the Propeptide from Human Preproapolipoprotein A-I on Co-Translational Translocation and Signal Peptidase Processing".
Journal of Biological Chemistry, 263, 3323–3327 (Mar. 5, 1988), Souciet et al., "Mutational Analysis of the Glutamine Phosphoribosylpyrophosphate Amidotransferase Pro-Peptide".

(List continued on next page.)

*Primary Examiner*—Douglas W. Robinson
*Assistant Examiner*—Jon P. Weber
*Attorney, Agent, or Firm*—Weiser & Stapler

[57] ABSTRACT

A method of making a biologically inactive polypeptide active is disclosed. Activity is imparted to the polypeptide through treatment with an exogenous peptide sequence. The nature of the exogenous peptide sequence is disclosed.

4 Claims, 9 Drawing Sheets

OTHER PUBLICATIONS

Journal of Biological Chemistry, 263, 12959–12963 (Sep. 15, 1988), Ikemura and Inouye, "In Vitro Processing of Pro-Subtilisin Produced in *Escherichia coli*".

Journal of Biological Chemistry, 263, 19771–19777 (Dec. 25, 1988), Wiren et al., "Importance of the Propeptide Sequence of Human Preproparathyroid Hormone for Signal Sequence Function".

Molecular Microbiology, 4(2), 295–304 (1990), Ohta and Inouye, "Pro-Subtilisin E: Purification and Characterization of its Autoprocessing to Active Subtilisin E in Vitro".

Pro. Natl. Acad. Sci. USA, 83, 3096–3100 (May 1986), Power et al., "Secretion and Autoproteolytic Maturation of Subtilisin".

PRODUCTION OF BIOLOGICALLY ACTIVE POLYPEPTIDES BY TREATMENT WITH AN EXOGENOUS PEPTIDE SEQUENCE

FIELD OF THE INVENTION

This invention relates to the production of biologically active proteins. The invention also relates to biologically active proteins. The invention utilizes an exogenous peptide sequence as an intermolecular catalyst for proper folding of the protein. Addition in trans of the exogenous peptide effectuates proper folding of inactive protein. The exogenous peptide can be the pro sequence of the expressed protein.

BACKGROUND OF THE INVENTION

In both prokaryotic and eukaryotic cells, some proteins are synthesized as longer precursors. These precursors require one or more proteolytic cleavages to generate an active, mature molecule. The precursor forms contain additional amino acids known as pre-and pro-sequences. Pre- and pro-sequences can be found singly or in combination in precursor molecules.

The pre-sequence is located at the N-terminus of the polypeptide chain and has been determined to be necessary for secretion and membrane localization. Generally, the pre-sequence (signal peptide) is 20 to 30 amino acids in length and contains a high content of hydrophobic residues. This precursor exists transiently. When the growing peptide chain is long enough for the signal peptide to extend beyond the ribosome, a cellular signal recognition particle binds the signal and the resultant particle/ribosome complex moves to the cell membrane. During binding of the complex to the membrane receptor, the signal recognition particle is displaced. As translation continues, the pre-sequence passes through the membrane and is followed by the rest of the nascent polypeptide chain. At a point when the protein is well inserted into the membrane, the signal sequence is cleaved off. After translation is complete, the protein has either passed entirely through the membrane (secretion) or is localized there (membrane bound). Removal of the signal sequence is the only cleavage necessary to generate the mature forms of secretory proteins like placental lactogen, lysozyme, ovomucoid, growth hormone and the viral membrane protein, VSV glycoprotein.

Most proteins, however, contain the additional prosequence. After cleavage of the pre-sequence, the resultant proprotein or prohormone exists as a stable precursor. Cleavage to generate the mature, active molecule may not occur until it is packaged in secretory vesicles. Many cells secrete toxins or potentially hazardous enzymes. It is thought that this delay in the production of an active protein protects the producing cell from the possible deleterious effects of the polypeptide produced. Examples of proteins which initially exist in the pro-form are albumin, insulin, parathyroid hormone and influenza virus hemagglutinin.

The function of the pro-sequence has not been well established. It is thought that this sequence may be required for the association of the pro-enzyme with the cell before release of the active enzyme into the medium and/or for guiding the proper folding of the protein into its active conformation. Recently, in the case of subtilisin E from *B. subtilis*, the covalently attached pro-sequence has been determined to be essential in guiding the proper folding of the protein to give active enzyme. (Ikemura et al, 1987, Ikemura and Inouye, 1988).

Many proteins have been cloned and overexpressed in heterologous systems. In some instances, these cloned proteins can be purified in a biologically active form using slight modifications of purification protocols worked out for natural sources of the protein. In other cases, the proteins produced exhibit diminished biological activity. Microscopic analysis of the host cell has indicated that large aggregates of these inactive proteins, called inclusion bodies, may form. The polypeptides exist in a non-native, inactive state within these aggregates. The aggregates are easily sedimented and can be dissociated by denaturing agents such as urea or guanidine hydrochloride. After dissociation, the protein must be renatured into its correct conformation. Successful renaturation techniques vary and are largely determined empirically. The problems associated with proper protein folding and the need for a more systematic approach has been recognized by the biotechnology industry and has spurred considerable research on protein folding (King, 1989).

It has been observed that in order to achieve maximum biological activity some proteins require their leader sequences to be cloned as well. It is thought that their inactivity which results from lack of a leader sequence is due to improper folding. The remedy of providing the leader sequence results in a final product having more amino acids than the natural product, where, in E. coli for example, the host cell lacks the ability to process these sequences off of the precursor molecule. The resultant protein may remain inactive until the prosequence is removed. Methods which exist to effect this removal have proved to be cumbersome.

The present invention provides a method for activation of polypeptides expressed without their prosequence or which have been partially or totally denatured in which an exogenous peptide sequence is added in trans to said polypeptides. The invention also provides the biologically active peptides.

BACKGROUND ART

A considerable amount of information has been published in the field of protein engineering. The enzyme subtilisin has proved to be an ideal model system for this field of study. Extensive enzymatic and x-ray crystallographic studies have been performed on this protein. Publications are noted here which deal with formation and stabilization of protein structure and precursor processing of subtilisin E and other proteins. All such references are hereby incorporated by reference.

ANFINSEN, C. B., "The Formation and Stabilization of Protein Structure," *Biochem. J.* 128, pp. 737–749 (1972) and ZABIN, I. and VILLAREJO, M. R., "Protein Complementation," *Ann. Rev. Biochem.* 44. pp. 295–313 (1975 , report on intermolecular effects on folding of proteins which do not require an extra prosequence for formation of a biologically active molecule.

POWER, S. D. et al., "Secretion and autoproteolytic maturation of Subtilisin," *Proc. Natl. Acad. Sci. USA* 83, pp. 3096–3100 (1986), have shown that a full-length precursor of subtilisin (preprosubtilisin) exists in association with the cell membrane. The conversion of the primary gene product into mature enzyme was shown to be mediated by active subtilisin. This processing was considered to be autocatalytic.

WONG, S.-L. and DOI, R. H., "Determination of the Signal Peptidase Cleavage Site in the Preprosubtilisin of *Bacillus subtilis.*" *J. Biol. Chem.* 261. pp. 10176–10181 (1986), precisely define the signal peptidase cleavage site in the preproenzyme. The signal peptide of pre-prosubtilisin was found to be twenty-nine amino acids in length.

IKEMURA, H., et al., "Requirement of Pro-Sequence for the Production of Active Subtilisin E in *Escherichia coli.*" *J. Biol. Chem.* 262, pp. 7859–7864 (1987 , elucidate the important role that the pro-sequence of pre-pro subtilisin plays in the formation of enzymatically active subtilisin. The authors propose that the pro-sequence is essential for guiding the appropriate folding of enzymatically active subtilisin E.

IKEMURA, H. and INOUYE, M., "In Vitro Processing of Prosubtilisin Produced in *Escherichia coli,* " J. Biol. Chem. 263, pp. 12959–12963 (1988), indicate that active subtilisin could not be renatured, once denatured in 6M guanidine-HCl. Pro-subtilisin dissolved in 6M guanidine-HCl could be renatured to produce active subtilisin. The cleavage of the pro-sequence which is essential for the production of active subtilisin occurs upon renaturation of pro-subtilisin. This processing was found to occur by a unimolecular, self-processing mechanism.

The references cited above do not disclose a process of producing biologically active polypeptides through use of an exogenous peptide (which is not part of mature protein) as an intermolecular catalyst for proper folding. Moreover, none of the background art makes it obvious than an exogenously added polypeptide (not part of mature protein) could effect the refolding of an inactive enzyme. The studies reviewed by Zabin and Villarejo reporting intermolecular effects on protein folding were not directed to proteins such as subtilisins which require an extra pro-sequence for formation of an active enzyme. In the protein complementation studies reported by these authors, the complementing polypeptide is one which is normally found in a subunit of the active enzyme. In the present invention, the exogenous peptide sequence which effects proper folding is not found in the mature protein. The present invention is thus a novel departure from the background art.

BACKGROUND AND INTRODUCTION

Subtilisin E is an alkaline serine protease produced by *Bacillus subtilis* (Boyer and Carton, 1968). These subtilisins have been widely used as model systems for protein engineering: improving the stability (Estell et al., 1985; Wells and Powers, 1986; Bryan et al., 1986; Pantoliano et al., 1987), changing substrate specificities (Estell et al., 1986; Wells et al., 1987; Cater and Wells, 1987), and pursuing structural and physiochemical characterization of the enzyme (Thomas et al., 1985; Russel et al., 1987). These studies have been performed by taking advantage of x-ray crystallographic data of the enzyme (Wright et al., 1969; Drenth et al., 1972) and its gene which has been cloned and sequenced (Stahl and Ferrari, 1984; Wong and Doi, 1986; Wells et al., 1983; Vasantha et al., 1984; Jacobs et al., 1985).

Subtilisins are produced from pre- pro-subtilisins consisting of the pre-sequence of 29 residues, the pro-sequence of 77 residues, and the mature protease of 275 residues (Stahl and Ferrari, 1984; Wong and Doi, 1986; Wells et al., 1983; Vasantha et al., 1984; Jacobs et al., 1985). Although the pre-sequence has been shown to function as the signal peptide for protein secretion across the membrane (Wong and Doi, 1986), the role of the pro-sequence has been obscure in the studies using Bacillus expression systems (Stahl and Ferrari, 1984; Wong and Doi, 1986; Powers et al., 1986; Byran et al., 1986; Wells et al., 1985). Recently, we have demonstrated the production of large amounts of the wild-type and mutant pro-subtilisins E in *Escherichia coli* by use of a high expression vector, pIN-III-ompA (Ikemura et al., 1987). In addition, we have established an in vitro system for processing of pro-subtilisin E produced in *E. coli* to active mature subtilisin E (Ikemura and Inouye, 1988). In the present study we used a crude pro-subtilisin preparation solubilized with guanidine-HCl, and demonstrated that the pro-sequence and subtilisin activity are both required for in vitro processing, and that the processing reaction occurs by an intramolecular, autoprocessing mechanism. We attempted to characterize further in vitro processing of pro-subtilisin E to active mature subtilisin E. For thus purpose, we first purified the wild-type pro-subtilisin E to homogeneity. Using the purified pro-subtilisin, we characterized the in vitro processing reaction under various conditions. Under the optimum conditions we were able to convert approximately 20% of pro-subtilisin to activate subtilisin. Our results demonstrate that the processing reaction is carried out by an intramolecular, autoprocessing mechanism.

SUMMARY OF THE INVENTION

Methods and compositions are provided for or promoting guiding of the appropriate folding of denatured protein molecules. After proper folding, these polypeptides have biological activity.

The invention provides for an exogenously added polypeptide which is not part of the final active protein. The polypeptide can be the pro-sequence of the denatured proteins, it may also include the pro-sequence plus additional amino acids. The source of the polypeptide may be natural or synthetic (including "genetically engineered").

The method of the invention provides for a combination of a denatured or improperly folded protein (i.e. one that is not active biologically) with the exogenous polypeptide. Intermolecular interaction between the two components elicits the proper folding of the inactive protein to the active form. The method results in a protein which has been made active not by natural means, but by "man-made" means. It is contemplated that this active folding process yielding the active protein can be accomplished both in vitro and in vivo.

The invention also contemplates applications of the process of the invention whereby activity is restored to "engineered", over-expressed proteins. Over-expression of proteins in prokaryotes can lead to aggregation. These aggregates are essentially inactive and require a denaturing agent for dissociation. It is contemplated for that after dissociation the method of the invention be used to restore or develop biological activity. Additionally, there are instances where it is undesirable to express a protein with its pro-sequence attached as it differs in activity from the native, mature form having the desired activity. It is also contemplated for the invention to allow expression of a protein without its pro-sequence yet ensure correct folding and high biological activity of the desired product.

DETAILED DESCRIPTION OF THE INVENTION

This invention relates to the use of an exogenous polypeptide to intermolecularly complement folding of denatured (or inactive) proteins into the active conformation. The polypeptide used to effect this reaction is not part of the final active protein. More specifically in a preferred embodiment of the invention, the activation of subtilisin E, an alkaline serine protease produced by *Bacillus subtilus* is described.

It has been shown in accordance with the invention that pro-subtilisin expressed from an *E. coli* high expression secretion vector dissolved in 6M guanidine-HCl could be renatured to produce active subtilisin. However, if subtilisin lacking the pro sequence is expressed from the same vector, it is inactive and could not be refolded to active subtilisin under the optimal conditions found for renaturation of denatured pro-subtilisin. (Ikemura and Inouye, 1988).

Figure 1:
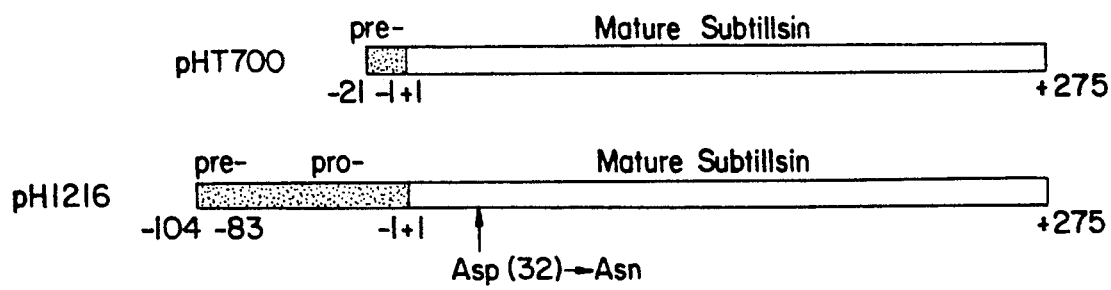
FIG. 1 shows the protein products from the subtilisin expression vectors, pHT700 and pHI216.

The method of the invention whereby an exogenous polypeptide is used to effect proper folding of a denatured protein comprises production of the exogenous polypeptide. In a specific embodiment of the invention, the exogenously added pro-sequence of subtilisin is obtained from the *E. coli* expression plasmid, pHI216 (FIG. 1). This plasmid is able to produce pro-subtilisin in which the aspartate residue at position 32 in the mature subtilisin was substituted with asparagine (Ikemura et al., 1987). Asp-32 is part of the active center triad, and its replacement results in a complete loss of the enzymatic activity (Powers et al., 1986). The polypeptide containing the pro-sequence is obtained from *E. coli* cell extracts by standard protein purification techniques (Ohta and Inouye, 1989 (in press)). Inactive subtilisin (lacking the pro-sequence) is obtained in a similar manner from the *E. coli* expression vector pHT700 (FIG. 1).

Varying amounts of denatured PHI216 pro-subtilisin are mixed with PHT700 subtilisin and dialyzed to remove the denaturing agent. After dialysis of about 3 hours, biological activity is produced in the PHT700 subtilisin. Activities regained after dialysis appear nearly proportional to the concentration of pHI216 pro-subtilisin added to the mixture, indicating a second order kinetic process.

In a preferred embodiment of the invention, the expressed inactive protein is denatured in 6M guanadine-HCl. The pHT700 subtilisin is denatured in 6M guanidine-HCl and after mixing with the exogenous sequence derived from pHI216, refolding efficiency (biological activity) is higher than when the denaturant is 5M urea. In the best mode of the invention, pre-incubation prior to dialysis of guanidine denatured expressed protein with the denatured exogenous intermolecular effector at temperatures around 20° C. for periods of 1 to 7 days is required. This results in optimal renaturation to active protein.

The molar ratios of exogenous sequence to denatured protein (R) are important. When inactive subtilisin (from pHT700) and the pro-sequence containing mutant protein (from pHI216) are combined at R values (pHI216/pHT700) of 0.2 to 2.5 and dialyzed immediately, after 2 to 3 hours of dialysis enzyme activity increased linearly up to an R value of approximately 1. When R was increased to 2.5, activity decreased to approximately 25% of the maximum observed at R equals 0.8. With a 7 day pre-incubation preceding dialysis, dramatic activation is observed at 2 to 3 hours after the start of dialysis for R values greater than 1. At R equals 1.2, the activity is twice that of the mixtures that were not pre incubated. For R values of 1.6 and 2.4, the enzyme activity further increased. These data suggest that there are at least 2 different modes of interaction between denatured subtilisin and its folding effector sequence. The first is observed without pre incubation at an R of less than one; the second is observed only when the mixture is pre-incubated at R values greater than one.

In another embodiment of the invention, intramolecular interaction of the effector sequence with denatured subtilisin Carlsberg and subtilisin BPN' can restore enzyme activity. The native enzymes were denatured at low pH, mixed with the exogenous sequence derived from pHI216 and pre-incubated at −20° C. for 7 days before dialysis. At R values of 1.2 and 2.4, specific activity was regained after three hours of dialysis.

The protein molecules described herein are not limited to those derived from subtilisin. It can readily be seen by those skilled in the art that various proteins can be activated by the process of the invention.

DETAILED DESCRIPTION OF THE FIGURES

Figure 5:
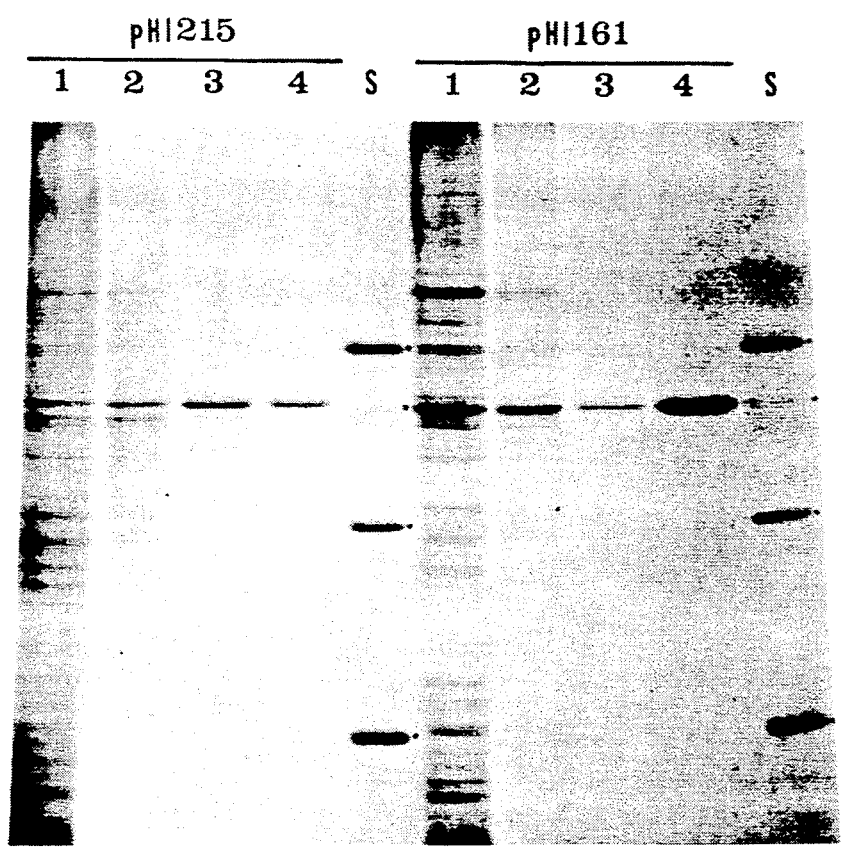
FIG. 5 shows a SDS-polyacrylamide gel electrophoresis of various pro-subtilisin E preparations.

FIG. 5 shows SDS-polyacrylamide gel electrophoresis of various pro-subtilisin E preparations from cells harboring pHI215 (wild-type) and pHI161 (mutant). Samples were applied to a 17.5% polyacrylamide gel. After electrophoresis the gel was stained with Coomassie Brilliant Blue. Purification was carried out as described under "Experimental Procedures." Lane 1, solubilized supernatant in 5M urea; lane 2, eluate from Sephacryl S-200 column chromatography; lane 3, eluate from CM-Sephadex C-50 column chromatography; lane 4, eluate from QAE-Sephadex Q-50 column chromatography. S indicates protein standards, and their molecular masses from top to bottom are 66, 45, 31, and 14 kDa.

Figure 6:
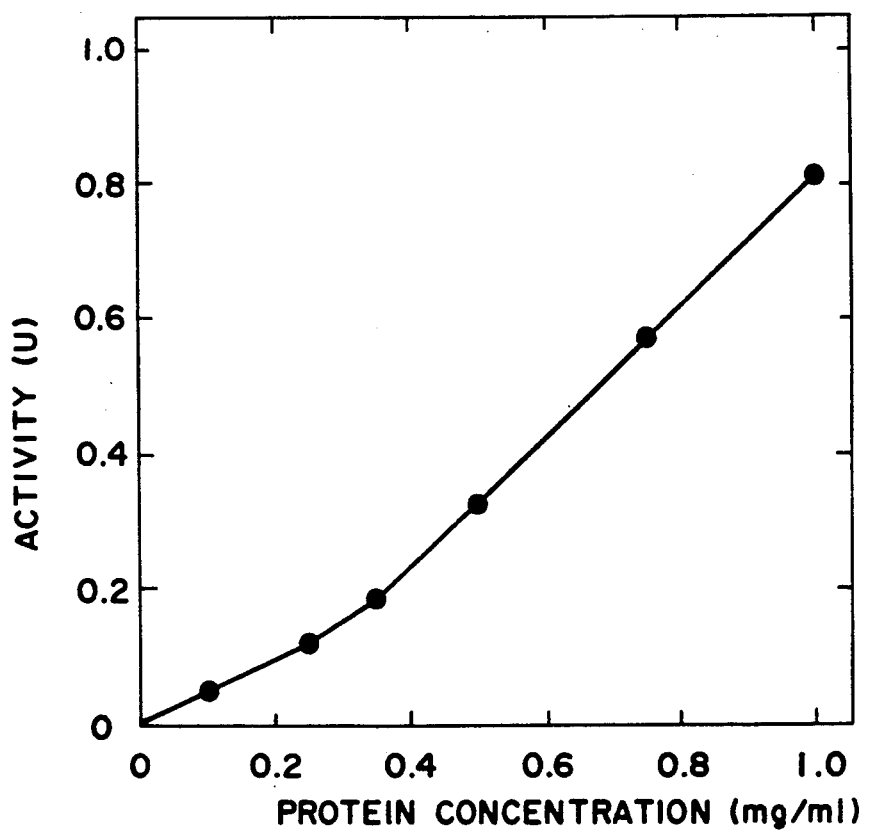
FIG. 6 shows in vitro processing of pro-subtilisin E from pHI215 in sodium phosphate buffer as a function of its protein concentration.

FIG. 6 shows in vitro processing of pro-subtilisin E from pHI215 in sodium phosphate buffer as a function of its protein concentration. Samples (0.1–1.0 mg protein/ml as indicated) were dialyzed against 0.2M sodium phosphate buffer (pH 6.2) at 4° C. for 2 hours. The subtilisin activity was determined as described under "Experimental procedures."

Figure 7:
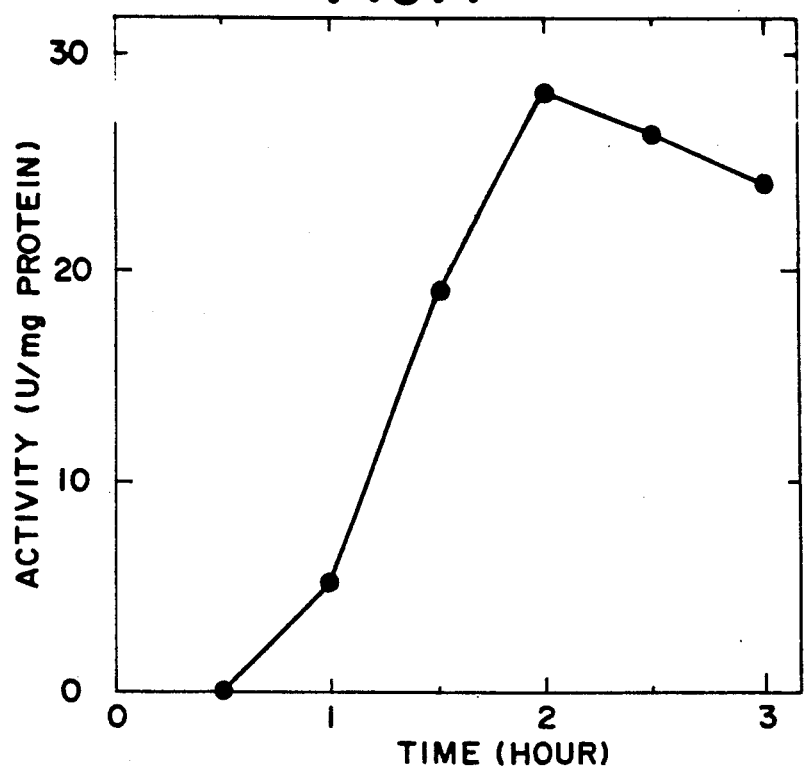
FIG. 7 shows the time course of in vitro processing of pHI215 pro-subtilisin E in sodium phosphate buffer.

FIG. 7 shows the time course of in vitro processing of pHI215 pro-subtilisin E in sodium phosphate buffer. Samples (0.4 mg protein/ml) were dialyzed against 0.2M sodium phosphate buffer (pH 6.2) at 4° C. for the times indicated. The subtilisin activity was measured as described under "Experimental Procedures."

Figure 8:
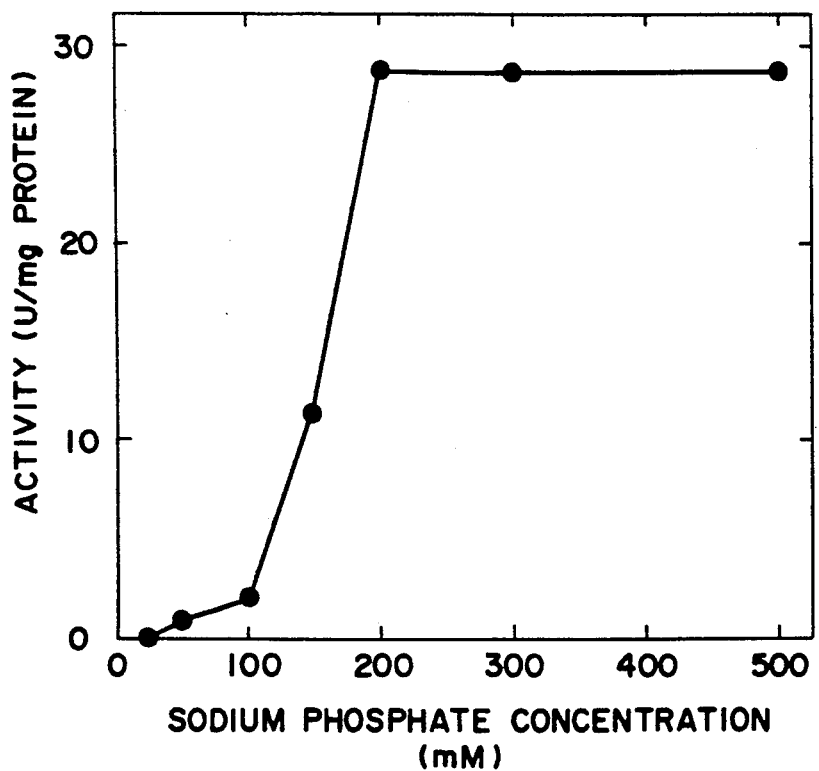
FIG. 8 shows the effect of the sodium phosphate buffer concentration on in vitro processing of pHI125 pro-subtilisin E.

FIG. 8 shows the effect of the sodium phosphate buffer concentration on in vitro processing of pHI215 pro-subtilisin E. Samples (0.4 mg protein/ml) were dialyzed against the indicated concentrations of sodium phosphate buffer (pH 6.2) at 4° C. for 2 hours. The subtilisin activity was measured as described under "Experimental Procedures."

Figure 9:
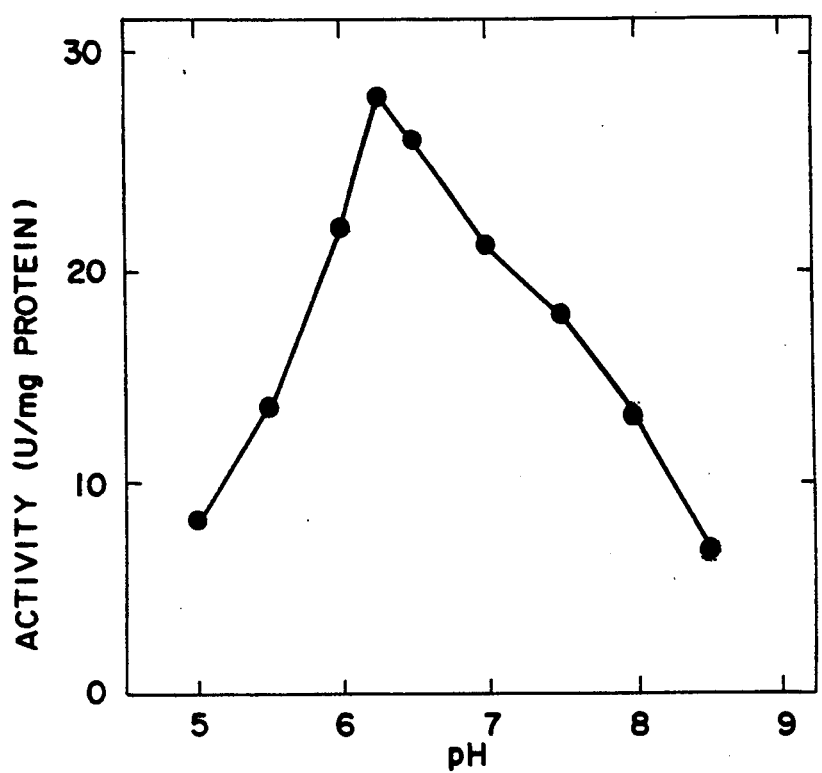
FIG. 9 shows the pH dependence of in vitro processing of pro-subtilisin E from pHI215 using sodium phosphate buffer.

FIG. 9 shows the pH dependence of in vitro processing of pro-subtilisin E from pHI215 using sodium phosphate buffer. Samples (0.4 mg protein/ml) were dialyzed against 0.2M sodium phosphate buffer at the indicated pH values at 4° C. for 2 hours. The subtilisin activity was determined as described under "Experimental Procedures."

Figure 10:
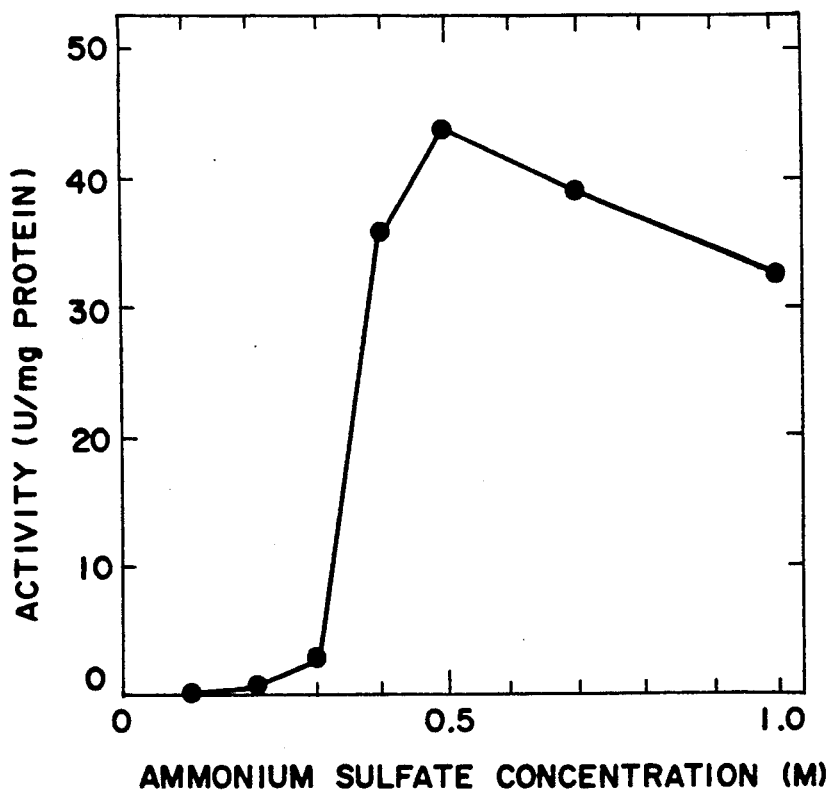
FIG. 10 shows the effect of ammonium sulfate on in vitro processing of pro-subtilisin E from pHI215.

FIG. 10 shows the effect of ammonium sulfate on in vitro processing of pro-subtilisin E from pHI215. Samples (0.4 mg protein/ml) were dialyzed against ammonium sulfate at the indicated concentrations in the presence of 10 mM sodium phosphate buffer (pH 6.2) at 4° C. for 2 hours. The subtilisin activity was determined as described under "Experimental Procedures."

Figure 11:
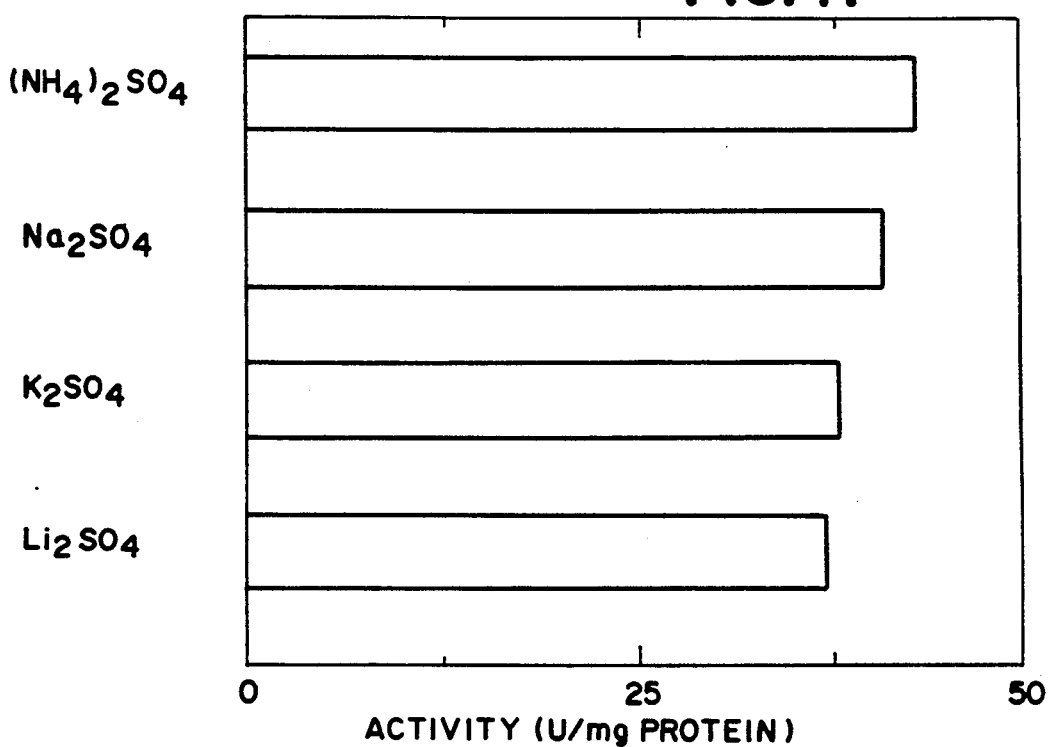
FIG. 11 shows the effect of various sulfates on in vitro processing of pro-subtilisin E from pHI215.

FIG. 11 shows the effect of various sulfates on in vitro processing of pro-subtilisin E from pHI215. Samples (0.4 mg protein/ml) were dialyzed against 0.5M ammonium sulfate, sodium sulfate, potassium sulfate or lithium sulfate in the presence of 10 mM sodium phosphate buffer (pH 6.25) at 4° C. for 2 hours. The subtilisin activity was measured as described under "Experimental Procedures."

Figure 12:
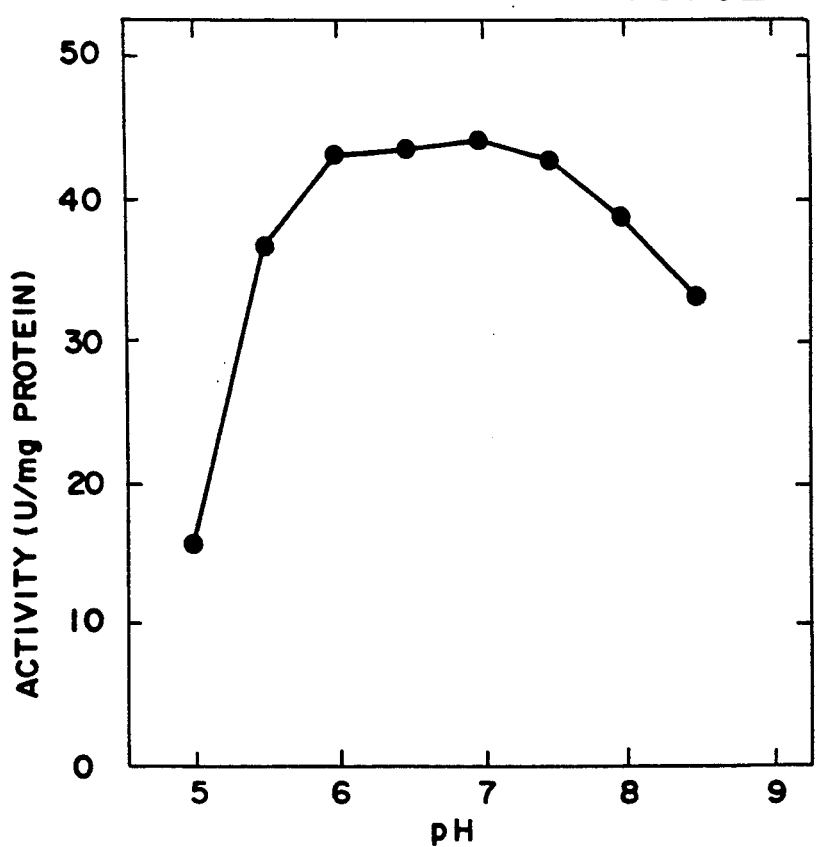
FIG. 12 shows the pH dependence of in vitro processing of pro-subtilisin E from pHI215 in ammonium sulfate.

FIG. 12 shows pH dependence of in vitro processing of pro-subtilisin E from pHI215 in ammonium sulfate. Samples (0.4 mg protein/ml) were dialyzed against 0.5M ammonium sulfate solution at 4° C. for 2 hours. pH was adjusted to the indicated values with 10 mM sodium phosphate buffer. The subtilisin activity was measured as described under "Experimental Procedures."

Figure 13:
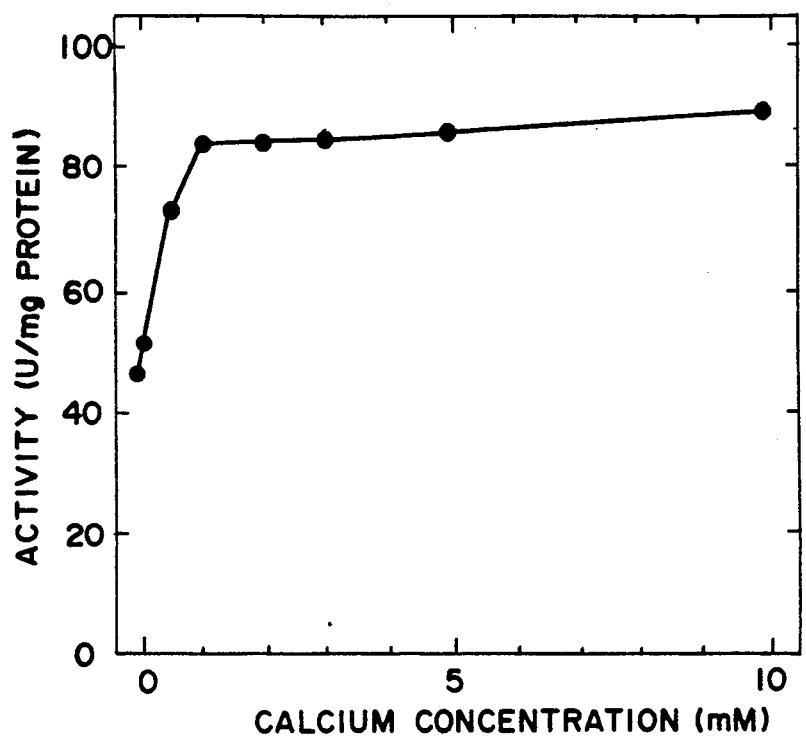
FIG. 13 shows the effect of calcium ion on in vitro processing of pro-subtilisin E from pHI215 in ammonium sulfate.

FIG. 13 shows the effect of calcium ion on in vitro processing of pro-subtilisin E from pHI215 in ammonium sulfate. Samples (0.4 mg protein/ml) were dialyzed against 0.5M ammonium sulfate-10 mM Tris-HCl buffer (pH 7.0) with or without $CaCl_2$ at the indicated concentrations at 4° C. for 2 hours. The subtilisin activity was determined as described under "Experimental Procedures."

Figure 14:
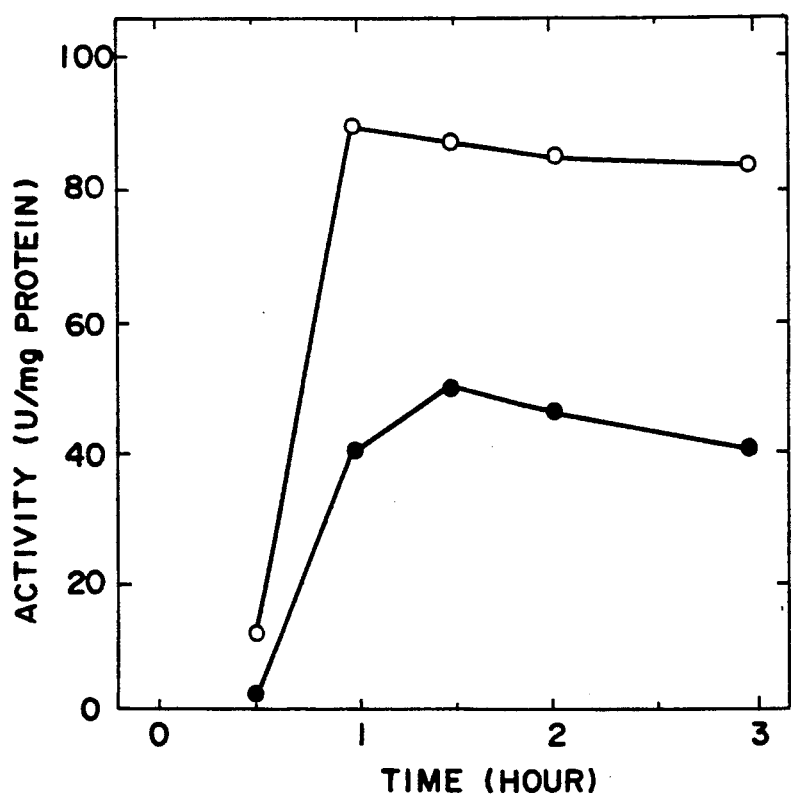
FIG. 14 shows the time course of in vitro processing of pro-subtilisin E from pHI215 in ammonium sulfate with or without $CaCl_2$.

FIG. 14 shows time course of in vitro processing of pro-subtilisin E from pHI215 in ammonium sulfate with or without $CaCl_2$. Samples (0.4 mg protein/ml) were dialyzed against 0.5M ammonium sulfate-10 mM Tris-HCl buffer (pH 7.0) with (O) or without (●) 1 mM $CaCl_2$ at 4° C. for the times indicated. The subtilisin activity was measured as described under "Experimental procedures."

Figure 15:
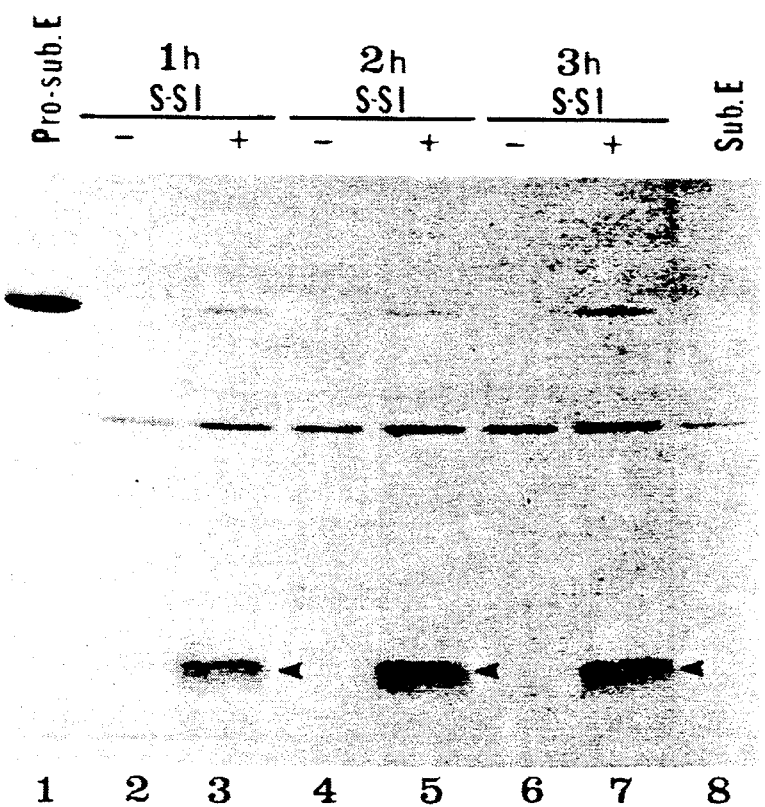
FIG. 15 shows the effect of S-SI on in vitro processing of pro-subtilisin E from pHI215.

FIG. 15 shows the effect of S-SI on in vitro processing of pro-subtilisin E from pHI215. Samples (0.43 mg = 12.2 nmoles) with or without S-SI (0.5 mg = 22.1 nmoles) were dialyzed against 0.5M ammonium sulfate-10 mM Tris-HCl buffer (pH 7.0) containing 1 mM $CaCl_2$ at 4° c. After incubation for the times indicated, dialysates were analyzed on a 17.5% polyacrylamide gel as described in FIG. 5. After electrophoresis, the gel was stained with Coomassie Brilliant Blue. Lane 1, pro-subtilisin E preparation before dialysis; lane 2, dialysate after 1 hour dialysis without S-SI; lane 3, dialysate after 1 hour dialysis with S-SI; lane 4, dialysate after 2 hours dialysis without S-SI; lane 5, dialysate after 2 hours dialysis with S-SI; lane 6, dialysate after 3 hours dialysis without S-SI; lane 7, dialysate after 3 hours dialysis with S-SI; lane 8, pure subtilisin E preparation. The arrowheads indicate the positions of S-SI.

In vitro Processing of Pro-subtilisin E purified from pHI215 and pHI161—In vitro processing of pro-subtilisin E to activate mature subtilisin E was examined using purified pro-subtilisin E preparations from pHI215 (wild-type) and pHI161 (mutant) under the same conditions used for a crude pHI215 pro-subtilisin E preparation extracted with 6M guanidine-HCl as described previously (Ikemura and Inouye, 1988). When purified pHI215 pro-subtilisin E (0.4 mg protein/ml) in 5M urea was dialyzed against 0.2M sodium phosphate buffer (pH 6.2) at 4° C. for 1 and 2 hours, the subtilisin activities at 1 and 2 hours dialysis were 4.8 and 28.2 U/mg pro-subtilisin, respectively. The maximum theoretical activity (if every pro-subtilisin molecule is converted to active subtilisin) is calculated to be 470 U/mg pro-subtilisin based on the activity of fully active subtilisin E (621 U/mg subtilisin) which was purified to homogeneity from $E.$ $coli$ cells carrying pHI212. Therefore, the processing efficiency at 2 hours dialysis is estimated to be 6%. In contrast, purified pHI161 pro-subtilisin E showed no protease activity at both 1 and 2 hours dialysis under the same conditions. When the dialysates from pHI215 and pHI161 were analyzed by SDS-polyacrylamide gel electrophoresis, pHI161 give no mature subtilisin E band, whereas the 2 hours dialysate of pHI215 showed not only the mature subtilisin band but also a clear band at around 13 kDa with two other faint protein bands at around 10 kDa (data not shown). These results are consistent with the previous report obtained with crude pro-subtilisin E extracts from pHI215 and pHI161 (Ikemura and Inouye, 1988). The present experiment with the purified pHI215 pro-subtilisin E further eliminates the possibility that the processing of pro-subtilisin to subtilisin is due to contaminating active subtilisin. It is also important to note that subtilisin cannot be renatured once denatured in 6M guanidine-HCl (Ikemura and Inouye, 1988). The fact that purified pro-subtilisin E from pHI161 ($Asp^{32}$ in the catalytic center of subtilisin was altered to Asn) could not be processed at all indicates that the function of $Asp^{32}$ is absolutely required for processing of pro-subtilisin E to active mature subtilisin E.

In Vitro Processing of pHI215 Pro-subtilisin E in Sodium Phosphate Buffer—We first examined if pro-subtilisin E concentration affects its processing efficiency. The solutions containing pHI215 pro-subtilisin E at various concentrations were dialyzed against 0.2M sodium phosphate buffer (pH 6.2) at 4° C. for 2 hours, and the results are shown in FIG. 6. The subtilisin activity increased almost linearly as the pro-subtilisin E concentration increased, indicating that the processing reaction is a unimolecular reaction. At the concentrations lower than 0.35 mg/ml, however, the processing efficiencies were lower than those at the concentrations higher than 0.35 mg/ml. These lower efficiencies at lower concentrations may be due to the stability of subtilisin E which may be concentration dependent. Accordingly, pro-subtilisin E was used at 0.4 mg/ml in all subsequent experiments.

In Vitro Processing of Pro-subtilisin E purified from pHI215 in Ammonium Sulfate—Sulfate ion has been demonstrated to protect the protein from unfolding (Vooedouw et al., 1976), and ammonium sulfate has been shown to be as effective for in vitro processing of pro-subtilisin E using a crude preparation extracted with guanidine-HCl as sodium phosphate buffer (Ikemura and Inouye, 1988). Hence, the effect of ammonium sulfate on processing of pro-subtilisin E to active mature subtilisin E was examined using pro-subtilisin E purified from pHI215.

For this purpose, pro-subtilisin E was dialyzed against ammonium sulfate at concentrations of 0.1 to 1.0M in the presence of 10 mM sodium phosphate buffer (pH 6.2) at 4° C. for 2 hours. As shown in FIG. 10, little or no subtilisin activity could be detected below 0.3M $(NH_4)_2SO_4$. However, a remarkable increase in activity was observed at 0.4M and the highest activity was obtained at 0.5M. This activity was approximately 1.5-fold higher than the highest activity obtained with sodium phosphate buffer (see FIG. 9). When the concentration was increased higher than 0.5M, the activity decreased again. When the samples dialyzed against the buffer containing greater than 0.5M ammonium sulfate were analyzed by SDS-polyacrylamide gel electrophoresis, the pro-subtilisin band was clearly detected (data not shown). This result indicates that ammonium sulfate at concentrations higher than 0.5M may inhibit the proper folding of pro-subtilisin to block the processing reaction.

Next, we examined the effect of cations of sulfates on the processing reaction. As shown in FIG. 11, at 0.5M there were no dramatic differences in the processing efficiency even if $NH_4^+$ was replaced by $Na^+$, $K^+$ or $Li^+$; $(NH_4)_2SO_4$ was most effective followed by $Na_2SO_4$, $K_2SO_4$, and $Li_2SO_4$ which was least effective. When the sulfate ion was replaced by $Cl^-$ at the same ionic strength (I=1.5), however, the processing efficiencies with KCl, NaCl, $NH_4Cl$ and LiCl were 54.3, 12.7, 6.2, and 4.0%, respectively, compared with $(NH_4)_2SO_4$ (data not shown). Thus, the order of the processing efficiency was quite different from that obtained with sulfate solutions (see FIG. 11). These results indicate that the sulfate ion of ammonium sulfate plays a major role in the in vitro processing of pro-subtilisin E.

The time course of in vitro processing of pro-subtilisin E was examined in 0.2M sodium phosphate buffer (pH 6.2). As shown in FIG. 7, the subtilisin activity could not be detected at all at 30 minutes. However, the activity sharply increased between 1 and 2 hours dialysis, and after 2 dialysis, the activity gradually dropped. This drop in activity may be due to autolysis of the processed active subtilisin E. The analysis of these samples by SDS-polyacrylamide gel electrophoresis revealed that the increased mature subtilisin band was proportional to the increasing subtilisin activity, and that after 2 hours dialysis, the pro-subtilisin band was no more detected (data not shown).

The effect of the sodium phosphate concentration on in vitro processing of pHI215 pro-subtilisin E is shown in FIG. 8. When pro-subtilisin E was dialyzed against various concentrations of sodium phosphate buffer (pH 6.2) at 4° C. for 2 hours, no subtilisin activity could be detected at 25 mM, and a slight subtilisin activity appeared at 50 and 100 mM. The sharp increase of the activity was observed between 100 and 200 mM, and the activity reached a plateau at 200 mM. This result confirms the previous result with a crude extract which showed that higher concentrations of sodium phosphate were required for the processing of pro-subtilisin to subtilisin (Ikemura et al., 1988). The substitution of sodium ion with potassium ion showed little effect on the processing efficiency.

The effect of pH on in vitro processing of pro-subtilisin E was then determined using 0.2M sodium phosphate buffer of various pHs for dialysis. As shown in FIG. 9, the pH dependence of the processing reaction was very sharp and the optimum pH was found to be 6.25

The pH dependence of in vitro processing of pro-subtilisin E was further determined in the system using 0.5M ammonium sulfate in 10 mM sodium phosphate buffer. In contrast to sodium phosphate used in FIG. 9, the pH dependence was broad and the optimum pH existed between 6 and 7.5 (FIG. 12).

The effect of urea on in vitro processing of pro-subtilisin E from pHI215 was also examined in 0.2M sodium phosphate buffer (pH 6.2). When pro-subtilisin E (0.4 mg protein/ml) was dialyzed against 0.2M sodium phosphate buffer (pH 6.2) containing various concentrations of urea at 4° C. for 2 hours, the recoveries of the subtilisin activity with 0.5, 1, 2, 3, 4, and 5M urea were 4.1, 1.4, 1.0, 0.9, 0.7 and 0%, respectively, of that without urea. Thus, 5M urea completely inhibited in vitro processing of pro-subtilisin E to active mature subtilisin E.

Effect of Calcium Ion on In Vitro Processing of Pro-subtilisin E purified from pHI215 Since calcium ion have been shown to be an important stabilizer in the structure of a number of proteolytic enzymes including subtilisin (Vooedouw et al., 1976; Pantoliano et al., 1988), the effect of calcium ion on in vitro processing of pro-subtilisin E was also examined. When pro-subtilisin E was dialyzed against 0.5M ammonium sulfate-10 mM Tris-HCl buffer (pH 7.0) containing various concentrations of $CaCl_2$ at 4° C. for 2 hours, a sharp increase in the subtilisin activity was observed at around 1 mM $CaCl_2$ (see FIG. 13). No further increase of the activity was observed at concentrations higher than 1 mM. The activity obtained after dialysis in the presence of 1 mM $CaCl_2$ was approximately 2 times higher than that in the absence of $CaCl_2$. In addition, when pro-subtilisin E was dialyzed against the same ammonium sulfate solution with or without 1 mM $CaCl_2$ for 0.5 to 3 hours, the maximum activity in the presence of $CaCl_2$ (88.6 U/mg pro-subtilisin) was obtained at 1 hour dialysis, whereas the mixture activity in the absence of $CaCl_2$ (49.2 U/mg pro-subtilisin) was observed after 1.5 hours dialysis (FIG. 14). Thus, the higher activation in the presence of $CaCl_2$ was found to occur much quicker than the activation in the absence of $CaCl_2$. The maximum activity obtained with 1 mM $CaCl_2$ is approximately 20% of the maximum theoretical recovery of subtilisin activity from the purified pro-subtilisin E (470 U/mg pro-subtilisin). All the renaturation experiments described above were carried out with pro-subtilisin E denatured in 5M urea. Hence, we further examined the recovery of active subtilisin E from purified pHI215 pro-subtilisin E denatured in 6M guanidine-HCl under optimum renaturation conditions. When purified pHI215 pro-subtilisin E in 5M urea was first dialyzed against 6M guanidine-HCl in 10 mM Tris-HCl buffer (pH 7.0) at 4° C. for 1 hour and then against 0.5M $(NH_4)_2SO_4$ in 10 mM Tris-HCl buffer containing 1 mM $CaCl_2$ at 4° C. for 1 hour, the final dialysate showed almost the same specific activity of subtilisin E as that obtained with the pro-subtilisin E denatured in 5M urea only. Under the same conditions, pHI161 pro-subtilisin E could not yield any enzymatic activity.

Effect of S-SI on In Vitro Processing of pHI215 Pro-subtilisin E—We have previously shown that Streptomyces subtilisin inhibitor (S-SI), a specific inhibitor for subtilisins (Murao and Sato, 1972, Sato and Murao, 1973 and 1974), could not block the processing of pro-subtilisin E in a crude extract (Ikemura and Inouye, 1988). We also repeated the experiment with the purified pHI215 pro-subtilisin E as follows. Pro-subtilisin E (0.43 mg=12.2 nmoles) was mixed with S-SI (0.5 mg=22.1 nmoles) in 0.05 ml in the presence of 5M urea, and the mixture was dialyzed against 0.5M ammonium sulfate-10 nM Tris-HCl buffer (pH 7.0) containing 1 mM $CaCl_2$ at 4° C. for 1, 2, and 3 hours. S-SI used was approximately 10 molar excess over pro-subtilisin E molecules because one S-SI molecule is known to bind to two subtilisin molecules (Sato and Murao, 1974). The analysis of these samples by SDS-polyacrylamide gel electrophoresis is shown in FIG. 15. In the samples dialyzed with S-SI the mature subtilisin E band as well as the pro-subtilisin E and S-SI bands are observed (lanes 3, 5 and 7). It is important to note that in spite of the fact that mature subtilisin E was produced by processing with S-SI, subtilisin activity was not detected in the dialysate. This indicates that S-SI completely inhibited the subtilisin activity even if the processing of pro-subtilisin E to subtilisin E was not blocked. From densitometric analysis of the processed subtilisin bands, the amounts of the mature subtilisin E produced at 1, 2, and 3 hours dialysis with S-SI were found to correspond to 69, 77, and 76% (on the molar basis) of that of pro-subtilisin E used for the experiment, respectively. Since 29, 22, and 22% of pro-subtilisin E used were found to remain unprocessed at 1, 2, and 3 hours dialysis, respectively, almost 100% of the pro-subtilisin E used could be accounted for at all time points. On the other hand, the amounts of the mature subtilisin E produced at 1, 2, and 3 hours dialysis without S-SI (lanes 2, 4, and 6) were found to correspond to 45, 51, and 51% (on the molar basis) of that pro-subtilisin E used for the experiment, respectively. This lower recovery without S-SI is likely due to autolysis of active subtilisin E, which can be prevented in the presence of S-SI. Furthermore, the fact that the amounts of the mature subtilisin E produced with S-SI were more than those produced without S-SI indicates that S-SI had no inhibitory effect on the processing reaction. The 20 to 30% of pro-subtilisin E remaining after processing with S-SI is most likely to have resulted from improper folding of pro-subtilisin E during the dialysis.

In the gel shown in FIG. 15, one cannot easily detect the pro-sequence fragment which results from the processing of pro-subtilisin E. When the sample prepared in the presence of S-SI was dialyzed against 6M guanidine-HCl again and applied to a column of Sephadex G-75 equilibrated with 6M guanidine-HCl-10 mM Tris-HCl buffer (pH 7.0), however, the fraction corresponding to the pro-sequence peptide was recovered (data not shown). We are currently characterizing the possible interaction between the cleaved pro-sequence peptide and the complex of subtilisin E and S-SI.

Conclusions. In the present work we have purified the wild-type pro-subtilisin E and the mutant pro-subtilisin E ($Asp^{32} \rightarrow Asn$) to homogeneity. The wild-type pro-subtilisin E in 5M urea was able to be refolded so that pro-subtilisin E can be processed to yield enzymatically active subtilisin E. However, the mutant pro-subtilisin E cannot be processed, indicating that the active site of subtilisin is essential for the processing. The present data also demonstrate unambiguously that the processing reaction occurs by an intramolecular, autoprocessing mechanism for the following reasons: (1) The processing reaction is a first-order reaction, and the efficiency of the conversion for pro subtilisin E to active subtilisin E is independent of the pro-subtilisin concentration (see FIG. 6). (2) S-SI has no effect on the processing reaction (see FIG. 15). (3) Denatured subtilisin E cannot be refolded to active subtilisin E under the conditions used for processing (Ikemura and Inouye, 1988). This eliminates the possibility that active subtilisin contaminated in the purified pro-subtilisin preparation is involved in the processing reaction.

The most efficient processing was obtained when the urea-denatured pro-subtilisin E was dialyzed against 0.5M $(NH_4)_2SO_4$ in 10 mM Tris-HCl (pH 7.0) containing 1 mM $CaCl_2$ for 1 hour. Under these conditions, 1 mg of pro-subtilisin E produced 89 U of the subtilisin activity. Since the theoretical maximum activity for 1 mg of pro-subtilisin E is estimated to be 470 U, the conversion efficiency of pro-subtilisin to active subtilisin is thus calculated to be approximately 20%, and the specific activity of the processed subtilisin is approximately a half of that of authentic subtilisin E. This low specific activity of processed subtilisin may be due to incomplete refolding of the subtilisin molecule and/or inactive subtilisin molecules contaminated in the active subtilisin fraction. This indicates that there are possibly many pathways for the refolding of denatured pro-subtilisin E. Some molecules are refolded into the right conformation which can be processed to active subtilisin, while other molecules are refolded into wrong conformations which cannot be processed to subtilisin.

Sulfate and phosphate ions were found to be much more effective on processing of pro-subtilisin E than $Cl^-$, $K^+$, $Na^+$, $Li^+$, and $NH_4^+$. This finding may be explained by stabilization of the protein based on the salting-out effectiveness of these ions as demonstrated by von Hippel and Wong (1964). Arakawa and Timasheff (1982) have shown that preferential hydration is involved in the stabilizing effect of $Na_2SO_4$ in concentrated solutions on the protein. Recently, Goto et al, (1988) have demonstrated that the stabilizing effect of $(NH_4)_2SO_4$ on $V_L$ and $C_L$ fragments of a immunoglobulin light chain denatured with guanidine-HCl is due to $SO_4^{2-}$ and largely due to an increase in hydrophobic interactions. For the structure of pro-subtilisin, it is reasonable to speculate on the basis of the tertiary structure of subtilisin determined by x-ray crystallography (Wright et al., 1969; Drenth et al., 1972) that the relatively large, rather hydrophobic area adjacent to the substrate-binding site is covered by the highly charged pro-sequence. This hydrophobic interaction between the prosequence and the hydrophobic area of the mature subtilisin may be facilitated by sulfate and phosphate ions, which stabilizes the structure of pro-subtilisin. When pro-subtilisin E was dialyzed against various concentrations of sodium phosphate or ammonium sulfate, a lag phase of the processing reaction and a sudden increase in the subtilisin activity at a certain high concentration were observed (see FIGS. 8 and 10). These findings indicate that ionic strengths of these salts play a critical role in refolding of denatured pro-subtilisin E and that high ionic strengths of these salts are required for the refolding of the denatured pro-subtilisin E. These phenomena may be related to the onset of the hydrophobic interaction between the pro-sequence and the mature subtilisin portion which is induced by high ionic strengths of phosphate and sulfate ions. In addition, the time course of an in vitro processing of pro-subtilisin E in 5M urea was examined in sodium phosphate or ammonium sulfate, a lag phase of the processing reaction and a sudden increase in the subtilisin activity were also observed (see FIGS. 7 and 14). These phenomena may be closely related to the concentration of urea remaining during dialysis. When urea concentration reaches below a critical concentration, denatured pro-subtilisin E is perhaps refolded suddenly. It is very intriguing to examine how the pro-sequence and subtilisin interact each other. The characterization of renatured pHI161 pro-subtilisin E and the interaction between the pro-sequence and subtilisin are now in progress.

ADDITIONAL RESULTS AND DISCUSSION

Purification of Pro-subtilisin E from pHI215 and pHI161—Since pro-subtilisins E were produced as aggregates in $E.\ coli$, they were first solubilized with guanidine-HCl as described previously (Ikemura and Inouye, 1988). Since guanidine-HCl interferes with ion-exchange chromatography, however, it was replaced by another denaturant, urea, which can be used during ion-exchange chromatography. It should be noted that the pro-subtilisin solution has to contain a denaturant, either guanidine-HCl or urea, in order to prevent autoprocessing to active subtilisin. The solubilized pro-subtilisin E in 5M urea from pHI215 or pHI161 was prepared as described under "Experimental Procedures" and gel-filtered on Sephacryl S-200 in the presence of 5M urea. The proenzyme was eluted near the void volume of the column, indicating that pro-subtilisin E treated with urea may exist as a complex. The gel-filtered pro-subtilisin E was then subjected to CM-Sephadex C-50 column chromatography, followed by QAE-Sephadex Q-50 column chromatography as described under "Experimental procedures". FIG. 5 shows SDS-polyacrylamide gel electrophoresis of various pro-subtilisin E preparations obtained from pHI215 and pHI161 during the purification procedures. The final co-subtilisin E preparations from pHI215 and pHI161 gave a single protein band (lane 4). One can notice that pro-subtilisin E from pHI215 migrates a little slower than that from pHI161. The difference in mobility seems to be due to the Asp to Asn mutation in the pHI161 pro-subtilisin E. A similar mobility difference has been observed in B. amyloliquefaciens subtilisin precursors (Powers et al., 1986). On the basis of the densities on the gel the final yields of pHI215 and pHI161 pro-subtilisin E were 1.25 and 1.20 mg/l of culture, respectively, which were 47 and 58% recovery from the crude extracts (lane 1) for pHI215 and pHI151, respectively.

The following examples are only given for purpose of illustration and not by way of limitation on the scope of the invention.

EXAMPLE 1

Time course of activation of inactive subtilisin produced from pHT700 by pHI216 pro-subtilisin.

Figure 2:
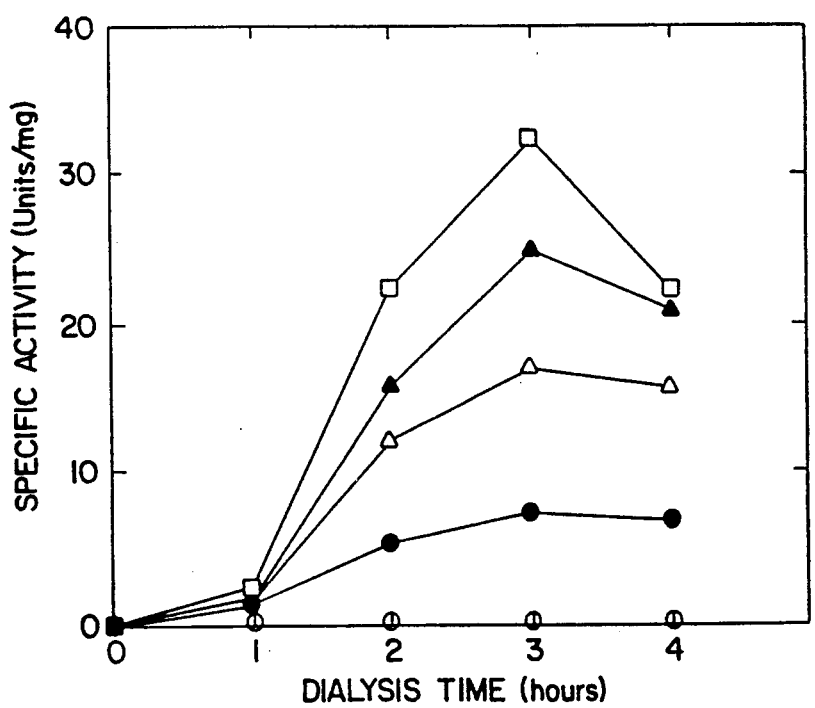
FIG. 2 shows a time course of activation of inactive subtilisin.

Purified pHT700 subtilisin (20 μl of 0.3 mg/ml) in 10 mM Tris-HCl (pH 7.0) containing 6M guanidine-HCl was mixed with 20 μl of purified pHI216 pro-subtilisin at different concentrations in 50 mM Tris-HCl (pH 8.1) containing 5M urea, then the mixture was dialyzed against 30 ml of 10 mM phosphate buffer (pH 7.1) containing 0.4M $(NH_4)_2SO_4$ using the drop dialysis technique as described previously. Aliquots were taken at the times indicated and subtilisin activity was assayed at 37° C. using succinyl-Ala-Ala-Pro-Phe p-nitroanilide as substrate (Ohta and Inouye, 1989 (in press)). One unit of activity was defined as the amount of enzyme that produced 1 μmol of p-nitroaniline per hour. Specific activities were calculated on the basis of the concentration of pHT700 subtilisin in the mixture. The concentration of pHI216 pro subtilisin solutions were as follows: (○) 0.0, (●) 0.08, (△) 0.16, (▲) 0.23 and (□) 0.32 mg/ml. The results (FIG. 2) indicate that, after 2 hours of dialysis, subtilisin activity was detected, and after 3 hours of dialysis, the activity reached the maximum levels. The activities regained after 3 hours of dialysis seem to be nearly proportional to the concentration of pHI216 pro-subtilisin added to the mixture. The results clearly demonstrate that pHI216 pro-subtilisin interacted with pHT700 subtilisin to guide its folding to form active subtilisin.

EXAMPLE 2

Dependence of activation of the denatured pHT700 subtilisin on the concentrations of the pHI216 pro-subtilisin.

Figure 3:
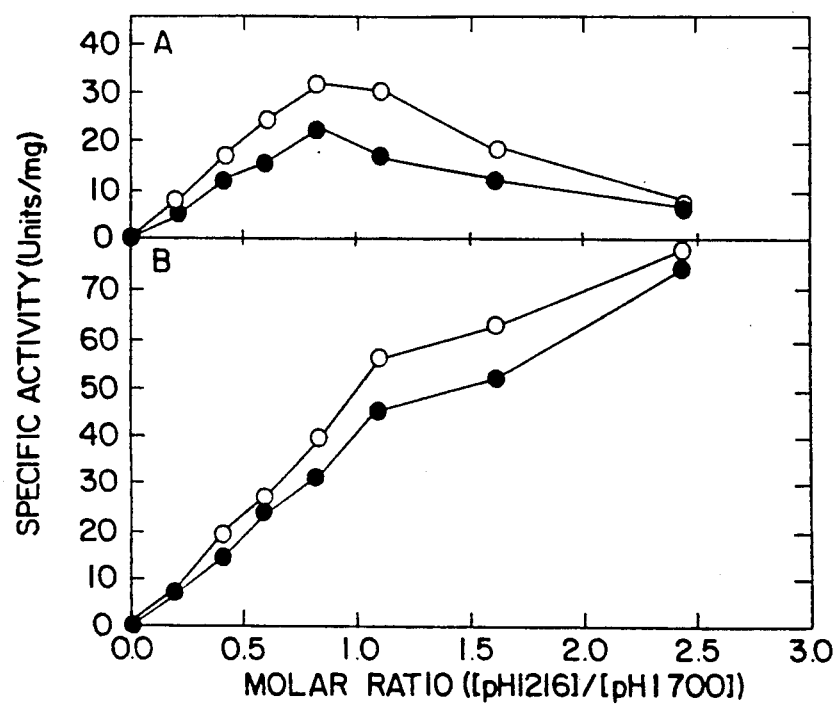
FIG. 3 shows the dependence of activation of denatured subtilisin on the concentration of pro-subtilisin.

The pHT700 subtilisin solution (15 μl of 0.3 mg/ml) in 10 mM Tris-HCl (pH 7.0) containing 6M guanidine-HCl was mixed with 15 μl of the pHI216 pro-subtilisin solution in 50 mM Tris-HCl (pH 8.1) containing 5M urea at the indicated molar ratio. These mixtures were then dialyzed for (●) two hours and (○) three hours, against 25 ml of 10 mM phosphate (pH 7.1) containing 0.4M $NH_4)_2SO_4$ (A) immediately after the two solutions were mixed, and (B) after the mixture was kept at −20° C. for 7 days. The enzymatic activity was measured as described in Example 1. The results (FIG. 3) indicate that pre-incubation of the mixture of denatured pHT700 subtilisin and denatured pHI216 pro-subtilisin makes a major contribution to optimal renaturation of pHT700 subtilisin, and that pHT700 subtilisin denatured in 6M guanidine-HCl is refolded more efficiently than that dissolved in 5M urea.

EXAMPLE 3

Renaturation of acid denatured subtilisins in the presence of the pHI216 pro-subtilisin.

Figure 4:
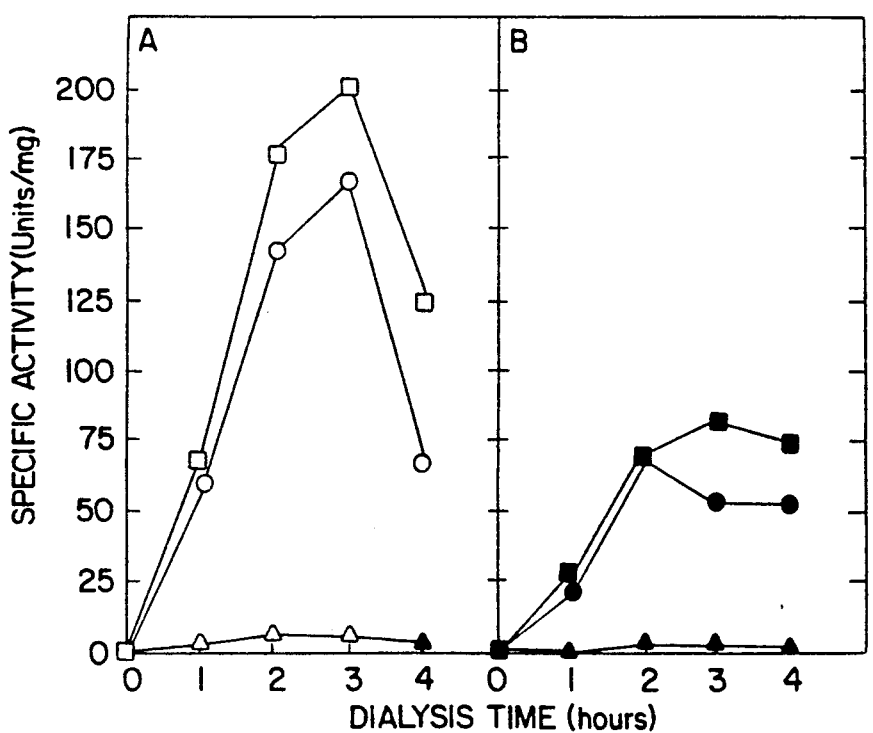
FIG. 4 shows the renaturation of acid denatured subtilisins in the presence of pro-subtilisin.

A, subtilisin Carlsberg (from Sigma) and B, subtilisin BPN' (from Boehringer) were dissolved in 50 mM citric acid and 10 mM boric acid solution (pH 2.2) to a final concentration of 0.3 mg/ml and then dialyzed against 10 mM Tris-HCl (pH 7.0) containing 6M guanidine-HCl. Fifteen μl of the acid denatured subtilisin solution was then mixed with 15 μl of the pHI216 pro-subtilisin solution in 50 mM Tris-HCl (pH 8.1) containing 5M urea. The resultant pH was always between 7 and 8. The concentrations of the pHI216 pro-subtilisin used were as follows; △ and ▲, 0.0 mg/ml; ○ and ●, 0.47 mg/ml; and □ and ■, 0.95 mg/ml. These mixtures were kept at −20° C. for 7 days and then dialyzed against 30 ml of sodium phosphate buffer (pH 7.1) containing 2 mM $CaCl_2$ and 0.5M $(NH_4)_2SO_4$. The enzymatic activity was measured as described in Example 1. The results (FIG. 4) indicate that both subtilisin Carlsberg and subtilisin BPN' showed little renaturation to active subtilisin without the addition of denatured pHI216 pro-subtilisin.

EXPERIMENTAL PROCEDURES

Materials—*E. coli* strain (hsdM+, trpE5, leuB6, lacY, recA/F', laqI$^q$, lac+ pro+) (Nakamura et al., 1982) was used as host cell. The isopropyl α-D-thio-galactopyranoside (IPTG) inducible pIN-III-ompA vector (Ghrayeb et al., 1984) was used for the expression and secretion of the wild-type and mutant pro-subtilisins E and the wild-type subtilisin E as previously described (Ikemura et al., 1987; Ikemura and Inouye, 1988). All the restriction enzymes used were from New England Biolabs, Bethesda Research Laboratories, International Biotechnologies, or Boehringer Mannheim and used as recommended by the suppliers. Guanidine-HCl, succinyl-L-Ala-L-Ala-L-Pro-L-Phe*p*-nitroanilide (subtilisin substrate), SephacrylS-200,CM-SephadexC-50, QAE-Sephadex Q-50, and the protein assay kit based on the Lowry method (Lowry et al., 1951) were from Sigma. CM-cellulose (CM-52) and urea were from Whatman and Bio-Rad, respectively. Streptomyces subtilisin inhibitor (S-SI) (Murao and Sato, 1972; Sato and Murao, 1973 and 1974) was a gift from Dr. Sato at the Biochemical Research Laboratory of Toyo Jozo Ltd., Shizuoka, Japan. All other chemicals were of reagent grade and were used without further purification.

Expression of the Subtilisin E in *E. coli*—Construction and the expression of plasmids pHI215 and pHI212 (wild-type) were described previously (Ikemura et al., 1987). The expression of pro-subtilisin E from pHI215 was performed at 37° C. in M9 medium (Miller, 1972) containing ampicillin (50 μg/ml) supplemented with Casamino Acids (2%). At a Klett reading of 80 with a red filter IPTG was added to the culture medium to a final concentration of 1 mM in order to induce gene expression. After 2 hours induction, the cells were harvested by centrifugation. Pro-subtilisin E produced from wild-type pHI215 (Ikemura et al., 1987) consists of the entire pro-sequence of 77 residues which is directly linked to the ompA signal peptide of the secretion vector, pIN-III-ompA. pHI161 (mutant) (Ikemura and Inouye, 1988) is identical to pHI215 except that a single-base mutation was introduced in the coding region of subtilisin E by oligonucleotide-directed site-specific mutagenesis which resulted in alteration of Asp at position 32 of the mature subtilisin E to Asn. $Asp^{32}$ is known to play an important role in the active site of the protease and its alteration of Asn has been shown to cause complete loss of the enzymatic activity (Powers et al., 1986). The expression of pro-subtilisin E from pHI161 was carried out under the same conditions as those used for pHI215. After 2 hours induction with IPTG at a final concentration of 1 mM the cells were harvested. pHI212 (Ikemura et al., 1987) is identical to pHI215 except that 6 additional residues exist between the ompA signal peptide and the pro-sequence. The expression of active subtilisin E from pHI212 was carried out as described previously (Ikemura et al., 1987; Takagi et al., 1988); at a Klett reading of 100, culture temperature was shifted down to 23° C. from 37° C. and then IPTG was added to the culture medium at a final concentration of 0.005 mM. After 3 hours induction at 23° C., the cells were harvested.

Solubilization and Purification of Pro-subtilisin E—Harvested cells harboring pHI215 and pHI161 from 3 liters of culture were suspended in 40 ml of ice-cold 10 mM Tris-HCl buffer (pH 7.0) and disintegrated by sonication using a sonicator model W-220F (Ultrasonic Inc.) The sonicated cells were centrifuged at 20,000×g for 10 minutes. Pro-subtilisin E which was produced as aggregates was recovered in the pellet and solubilized in 15 ml of ice-cold 6M guanidine-HCl in 10 mM Tris-HCl (pH 7.0) as described previously (Ikemura and Inouye, 1988). After incubation at 4° C. for 2 hours, the insoluble materials were removed by centrifugation at 100,000×g for 40 minutes. The supernatant was then dialyzed against 100 volumes of 50 mM sodium-potassium phosphate buffer (Na-K phosphate buffer) (pH 5.0) containing 5M urea at 4° C. overnight. The dialysate was centrifuged at 100,000×g for 40 minutes and the solubilized pro-subtilisin E was recovered in the supernatant. All subsequent steps were conducted at 4° C.

The purification of pro-subtilisin E from pHI215 was carried out as follows. The solubilized supernatant (15 ml) was applied to a column of Sephacryl S-200 (2.5×114 cm) equilibrated with 50 mM Na-K phosphate buffer (pH 5.0)-5M urea. The pro-enzyme was eluted from the column with the equilibrating buffer. Fractions with the pro-enzyme were pooled and then directly applied to a column of CM-Sephadex C-50 (1.5×15 cm) equilibrated with the same buffer as used for gel filtration on Sephacryl S-200. The column was washed with the equilibrating buffer until protein was no longer detectable in the effluent. The elution of the pro-enzyme from the column was then carried out with a 150 ml linear gradient of 0 to 0.3M NaCl in the equilibrating buffer. The pro-enzyme was eluted from the resin between 0.15 and 0.2M NaCl and fractions with the pro-enzyme were pooled. After concentration with an Amicon ultrafiltration apparatus using a YM 10 membrane, the pooled solution (4.5 ml) was dialyzed against 100 volumes of 50 mM Tris-HCl buffer (pH 8.1) containing 5M urea. The dialysate was loaded onto a column of QAE-Sephadex Q-50 (1.5×1.5 cm) equilibrated with the same buffer as that used for dialysis. After washing of the column with the equilibrating buffer, the elution of the pro-enzyme was performed with a 100 ml linear gradient of 0 to 0.1M NaCl in the equilibrating buffer. The pro-enzyme containing fractions were pooled and concentrated to 2 ml in the Amicon ultrafiltration system using a YM 10 membrane. The concentrated pro-enzyme preparation was again dialyzed against 150 volumes of 10 mM Tris-HCl buffer (pH 7.0)-5M urea and stored at −20° C. until use.

The purification of pro-subtilisin E from pHI161 was carried out as follows. The gel filtration of the solubilized supernatant (15 ml) on Sephacryl S-200 was conducted under the same conditions as those used for pHI215. The pro-enzyme containing fractions were pooled and subjected to a column of CM-Sephadex C-50 (1.5×1.5 cm) under the same conditions as used for pHI215. After washing the column with the equilibrating buffer (50 mM Na-K phosphate buffer (pH 5.0)-5M urea) the elution of the pro-enzyme from the column was carried out with a 150 ml linear gradient of 0 to 0.5M NaCl in the equilibrating buffer. The pro-enzyme was eluted between 0.35 and 0.42M NaCl and fractions with the pro-enzyme were pooled and concentrated to 4 ml in the Amicon ultrafiltration system using a YM 10 membrane. The concentrated solution was dialyzed against 100 volumes of 50 mM Tris-HCl buffer (pH 8.5) containing 5M urea. The dialysate was applied to a column of QAE-Sephadex Q-50 (1.5×1.5 cm) equilibrated with the same buffer as used for dialysis. After washing the column with the equilibrating buffer the elution of the pro-enzyme was performed with 100 ml linear gradient of 0 to 0.1M NaCl in the equilibrating buffer. The pro-enzyme was eluted between 0.05 and 0.06M NaCl. The eluate was concentrated to 1 ml with the Amicon ultrafiltration apparatus using a YM 10 membrane. The concentrated solution was dialyzed against 150 volumes of 10 mM Tris-HCl buffer (pH 7.0) containing 5M urea and stored at −20° C. until use. Pro-subtilisin E was analyzed during the purification procedures by sodium dodecyl sulfate (SDS)-polyacrylamide gel electrophoresis using a 17.5% polyacrylamide as described previously (Ikemura et al., 1987).

Purification of Subtilisin E—Active subtilisin E from pHI212 was purified using a CM-52 column as described previously (Ikemuar et al., 1987). The purified preparation was further gel-filtrated on Sephadex G-75 (Pharmacia) to remove autolyzed products. Subtilisin E activity was assayed spectrophotometrically in 50 mM Tris-HCl buffer (pH 8.5)-1 mM $CaCl_2$ at 37° C. according to the method of DelMar et al. (1979) using 0.13 mM succinyl-L-Ala-L-Pro-L-Phe $p$-nitroanilide as substrate as described previously (Ikemura et al., 1987). The activity was calculated as units/mg protein. One unit (U) is defined as the activity releasing 1 $\mu$mol of $p$-nitroaniline per hour.

Processing of Pro-subtilisin E to Active Subtilisin E—An appropriate volume of purified pro-subtilisin E preparation (dissolved in 10 mM Tris-HCl buffer (pH 7.0)-5M urea) was dialyzed against 1,000 volumes of various dialyzing solutions at 4° C. for specified times by the drop dialysis technique (Marusyk and Sergeant, 1980) using a VMWP membrane filter (0.05 $\mu$M Millipore). After dialysis, the exact volume of the dialysate was measured to calibrate the volume change during dialysis. The dialysate was analyzed for protease activity as well as by SDS-polyacrylamide gel electrophoresis to estimate the conversion of pro-subtilisin to subtilisin. Protease activity was measured under the same conditions as described above. The protease activity was expressed as units/mg protein of pro-subtilisin E used for each processing experiment. The analysis of the dialysate by SDS-polyacrylamide gel electrophoresis was performed under the same conditions as used for pro-subtilisin E analysis described above. After electrophoresis, if necessary, protein bands stained with Coomassie Brilliant Blue were scanned using a Hoeffer scanning densitometer and their amounts were quantitated by the GS-360 Hoeffer Data System.

Protein Determination—Protein was measured by the method of Lowry et al. (1951) using bovine serum albumin as standard.

There are other subtilisins produced by various species of Bacillus which are known, for instance subtilisin BPN' from *B. amyloliquefaciens*, subtilisin Carlsberg from *B. licheniformis* and *B. pumilis*, and subtilisin Amylosacchariticus from *B. amylosacchariticus*. Such subtilisin may likewise be biologically activated in accordance with the process of the invention.

The purification and characterization of the autoprocessing to active subtilisin E in vitro is described in the below-referred to reference of OHTA, Y. and INOUYE, M. which is incorporated herein by reference and made a part hereof.

Other proteins may likewise be biologically activated in accordance with the process described above.

REFERENCES

Arakawa and Timasheff (1982), *Biochemistry*, 21:6545-6552.
Boyer and Carton (1968), *Arch. Biochem. Biophys.*, 128:442-455.
Bryan et al. (1986), *Proc. Natl. Acad. Sci. USA*, 93:3743-3745.
Bryan et al. (1986), *Protein:Struc., Funct., Genetc.*, 1:326-334.
Cater and Wells (1987), *Science*, 237:394-399.
DelMar et al. (1979), *Analyt. Biochem.*, 99:316-320.
Drenth et al. (1972), *Eur. J. Biochem.*, 26:177-181.
Estell et al. (1985) *J. Biol Chem.*, 260:6518-6521.
Estell et al. (1986), *Science*, 233:650-663.
Ghrayeb et al. (1984), *EMBO J.*, 3:2437-2442.
Goto et al. (1988), *Biochemistry*, 27:1670-1677.
Jacobs et al. (1985), *Nucl. Acids Res.*, 13:8913-8922.
Lowry et al. (1951), *J. Biol. Chem.*, 193:265-275.
Markland and Smith (1971), *The Enzymes*, Vol. 3, Academic Press, pps. 561-608.
Marusyk and Sergeant (1980), *Anal. Biochem.*, 105:403-404.
Miller (1972), *Experiments in Molecular Genetics*, Cold Spring Harbor, New York: Cold Spring Harbor Laboratory Press, pp. 431-432.
Murao and Sato (1972), *Agric. Biol. Chem.*, 36:160-163.
Nakamura et al. (1982), *J. Mol. Appl. Genet.*, 1:289-299.
Pantoliano et al. (1987), *Biochemistry*, 26:2077-2082.
Pantoliano et al.(1988), *Biochemistry*, 27:8311-8317.
Russel et al. (1987), *J. Mol. Biol.*, 193:803-813.
Sato and Murao (1973), *Agric. Biol. Chem.*, 37:1067-1072.
Sato and Murao (1974), *Agric. Biol. Chem.*, 38:2227-2233.
Stahl and Ferrari (1984), *J. Bacteriol.*, 158:411-418.
Takagi et al. (1988), *Bio/Technology*, 6:884-950.
Thomas et al. (1985), *Nature*, 318:375-376.
Vasantha et al. (1984), *J. Bacteriol.*, 159:811-819.
von Hippel and Wong (1964), *Science*, 145:577-580.
Vooedouw et al. (1976), *Biochemistry*, 15:3716-3724.
Wells et al., (1983), *Nucleic Acid Res.*, 11:7911-7925.
Wells and Powers (1986), *J. Biol. Chem.*, 261:6554-6570.
Wells et al. (1987), *Proc. Natl. Acad. Sci. USA*, 84:1219-1223.
Wells et al. (1985), *Gene Amst.*, 34:315-323.
Wright et al. (1969), *Nature*, 221:235-242.

We claim:

1. An in vitro method for producing a biologically active polypeptide from a biologically inactive polypeptide which is lacking its pro-sequence and is irreversibly unfolded into a biologically inactive conformation, which method comprises intermolecularly interacting the biologically inactive polypeptide with an effective amount of the pro-sequence of the naturally occurring polypeptide and promoting the folding of the biologically inactive polypeptide into its corresponding mature biologically active polypeptide.

2. The method of claim 1 i which the inactive polypeptide is subtilisin and the corresponding mature folded product is its biologically active form.

3. The process of claim 1 wherein the interacting is carried out by incubating together in an aqueous solution the inactive polypeptide and the pro-sequence.

4. The method of claim 1 wherein the pro-sequence is synthetic.

* * * * *